United States Patent [19]

Rhodes

[11] Patent Number: 5,922,956
[45] Date of Patent: Jul. 13, 1999

[54] DYNAMIC ULTRASONIC RESONANCE TESTING

[76] Inventor: George W. Rhodes, 100 Camino de la Paloma, Corrales, N.M. 87948

[21] Appl. No.: 08/880,341

[22] Filed: Jun. 23, 1997

[51] Int. Cl.$^6$ .................................................. G01N 29/12
[52] U.S. Cl. .............................................. 73/579; 73/602
[58] Field of Search ........................ 73/579, 602; 702/56

[56] References Cited

U.S. PATENT DOCUMENTS 4,322,806  3/1982  Allison ..................................... 702/76
4,976,148  12/1990  Migliori et al. ........................... 73/579

OTHER PUBLICATIONS

Hewlett Packard Signal Analyzers, Model 3582A, 1986 Catalog, pp. 701–702.

*Primary Examiner*—John E. Chapman
*Attorney, Agent, or Firm*—Ray G. Wilson

[57] ABSTRACT

Relevant resonance response characteristics of a sample are determined for use in characterizing the sample for non-destructive testing. The sample is excited by an exciting mechanical input at a plurality of ultrasonic frequencies. The response is separated into in-phase and quadrature components and the resonance response characteristics are computed from the in-phase and quadrature components. Apparatus for obtaining the relevant response characteristics includes a frequency generator for inputting an exciting ultrasonic frequency to the sample. A transducer outputs a response of the sample to the exciting ultrasonic frequency. A dynamic signal analyzer is connected to receive the response of the sample and to output in-phase and quadrature components of the response of the sample. A computer then determines the relevant response characteristics from the in-phase and quadrature components.

14 Claims, 7 Drawing Sheets

DYNAMIC ULTRASONIC RESONANCE TESTING

BACKGROUND OF THE INVENTION

This invention relates to non-destructive testing (NDT), and, more particularly, to resonant ultrasound spectroscopy (RUS) to detect defective parts.

RUS is a non-destructive technique for detecting defective parts that occur in a manufacturing process or that develop defects during use. The technique generally involves generating a response to an input frequency, where the input frequency is swept over a range of frequencies and the output is characterized by a resonant amplitude response spectrum. The resonant amplitude response spectrum of an acceptable part is characterized by a variety of criteria in the prior art, which characterizations are enhanced by the present invention.

A major problem has plagued RUS in its ability to reliably detect a defective or flawed object. This problem relates to the separation, measurement and identification of key resonant responses for use in the characterizations. In many circumstances, it is difficult to reliably identify the desired key resonances in a spectrum in which many resonances are present. There are two reasons for this:

1. All solid objects have very large numbers of mechanical resonances. For example, a 1 inch diameter ball may have 1000 possible resonances, limited only by the dissipation or attenuation of sound. At higher frequencies, the resonance responses run together and strongly overlap in a manner where it is neither desirable nor necessary to attempt to separate them for the purposes of flaw detection. At frequencies below this limit (called the reverberation limit) where RUS NDT is executed, resonance responses are more distinguishable. But it is frequently the case that the important resonances are near each other and are also near resonances that are not important to the test. Amplitude response spectra are not able to identify resonances by any characterization other than frequency and amplitude and this leads to ambiguities in interpreting resonance spectra.

2. Some resonance responses are weak because the transmitting transducer or the receiving transducer has a weak output or response mode that is located near a node or region of weak vibration of a particular mode of the part. In order to find such weak resonances many tests can be used, including a full mathematical least squares fitting of all the data. However, in a production environment, this is not practical and the user must rely on very fast, but not rigorous, pattern recognition to detect the presence of a resonance. Such routines become less and less reliable the weaker the resonance response. Important resonance response peaks that are weak need to be distinguished from the background and the frequency of the peak must be determined from the weak response data.

Accordingly, it is an object of the present invention to provide a characterization of resonant responses that enable resonance responses to be more particularly distinguished.

It is another object of the present invention to provide a method for allocating a frequency and amplitude to a weak response.

One other object of the present invention is to increase the reliability of RUS to distinguish acceptable parts from flawed or defective parts.

Additional objects, advantages and novel features of the invention will be set forth in part in the description which follows, and in part will become apparent to those skilled in the art upon examination of the following or may be learned by practice of the invention. The objects and advantages of the invention may be realized and attained by means of the instrumentalities and combinations particularly pointed out in the appended claims.

SUMMARY OF THE INVENTION

To achieve the foregoing and other objects, and in accordance with the purposes of the present invention, as embodied and broadly described herein, this invention may comprise a method for determining relevant resonance response characteristics for use in characterizing a sample for non-destructive testing. The sample is excited by an exciting mechanical input at a plurality of ultrasonic frequencies. The response is separated into in-phase and quadrature components and the resonance response characteristics are computed from the in-phase and quadrature components.

In another characterization of the present invention, apparatus is provided for determining relevant resonance response characteristics for use in characterizing a sample. In a preferred embodiment, the apparatus includes a frequency generator for inputting an exciting ultrasonic frequency to the sample. A transducer outputs a response of the sample to the exciting ultrasonic frequency. A dynamic signal analyzer is connected to receive the response of the sample and to output in-phase and quadrature components of the response of the sample. A computer then determines the relevant response characteristics from the in-phase and quadrature components.

BRIEF DESCRIPTION OF THE DRAWINGS

The accompanying drawings, which are incorporated in and form a part of the specification, illustrate embodiments of the present invention and, together with the description, serve to explain the principles of the invention. In the drawings.

DETAILED DESCRIPTION

The present invention recognizes that the response of a sample to an exciting frequency includes both an amplitude component and a phase component. The phase component has generally not been used on RUS, but I have recognized that phase can be used to characterize resonance responses and also to locate resonance response peak center frequency values and determine peak amplitude values at the center frequency.

Figure 1:
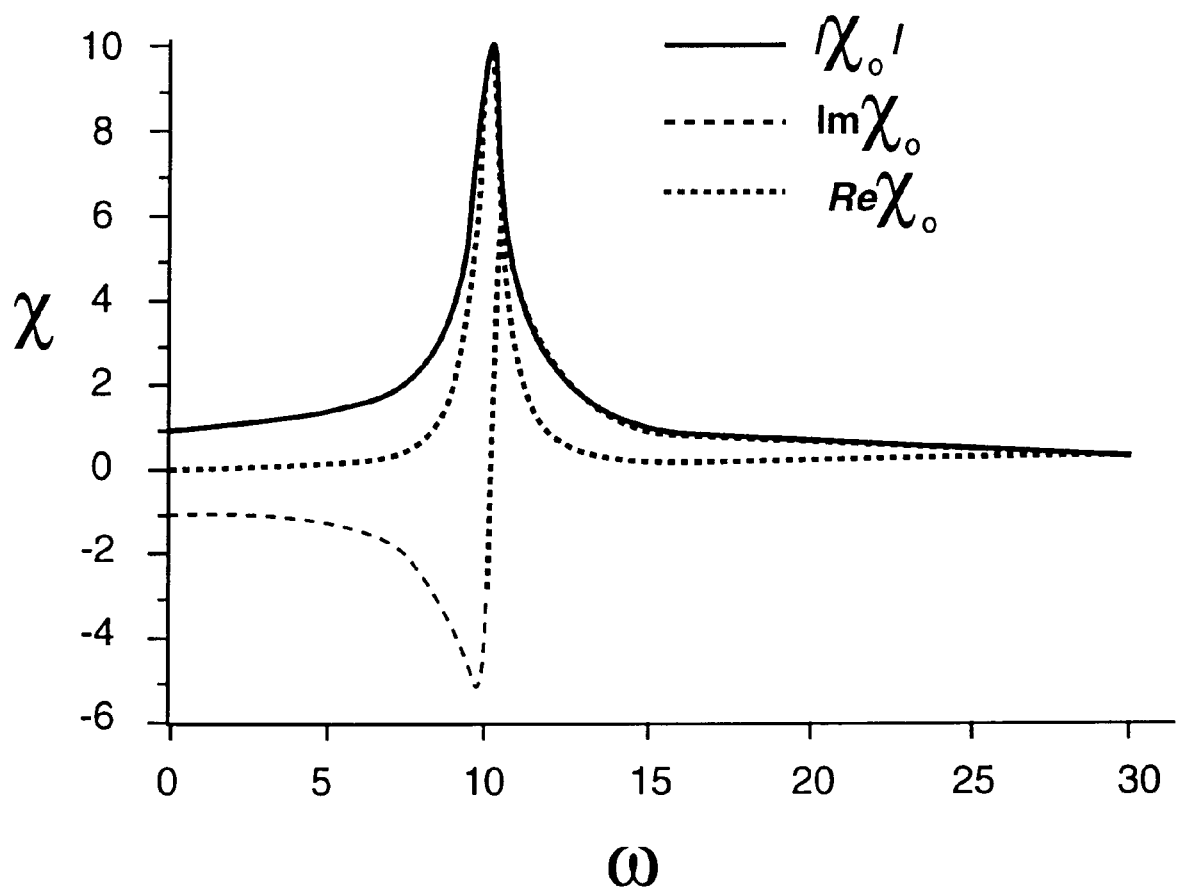
FIG. 1 is an exemplary resonance response showing the contributions of the in-phase and quadrature components.

A single amplitude x(t) for the mechanical resonance response can be represented by a complex function known as a Lorentzian:

$$x(t) = x_o(\omega)e^{-i\omega t}, \text{ where } x_o(\omega) = \frac{iA\omega\omega_o/Q}{\omega^2 - \omega_o^2 + i\omega\omega_o/Q},$$

where $\omega$ is $2\pi$ times the exciting frequency, $\omega_o$ is $2\pi$ times the frequency of the resonance, Q is the center frequency of the resonance divided by the full width of the bandwidth of the resonance response at the half amplitude points, and A is the maximum amplitude of x at the peak of the resonance. Thus, $x_o(\omega)$ has both a real (in-phase) component and an imaginary (quadrature or out-of phase) component. FIG. 1 graphically depicts the amplitude of $|x_o(\omega)|$, Re $x_o(\omega)$ and Im $x_o(\omega)$ as a function of frequency for a simple driven resonator with Q=10 and a center resonance frequency of $\omega_o=10/2\pi$.

Figure 2:
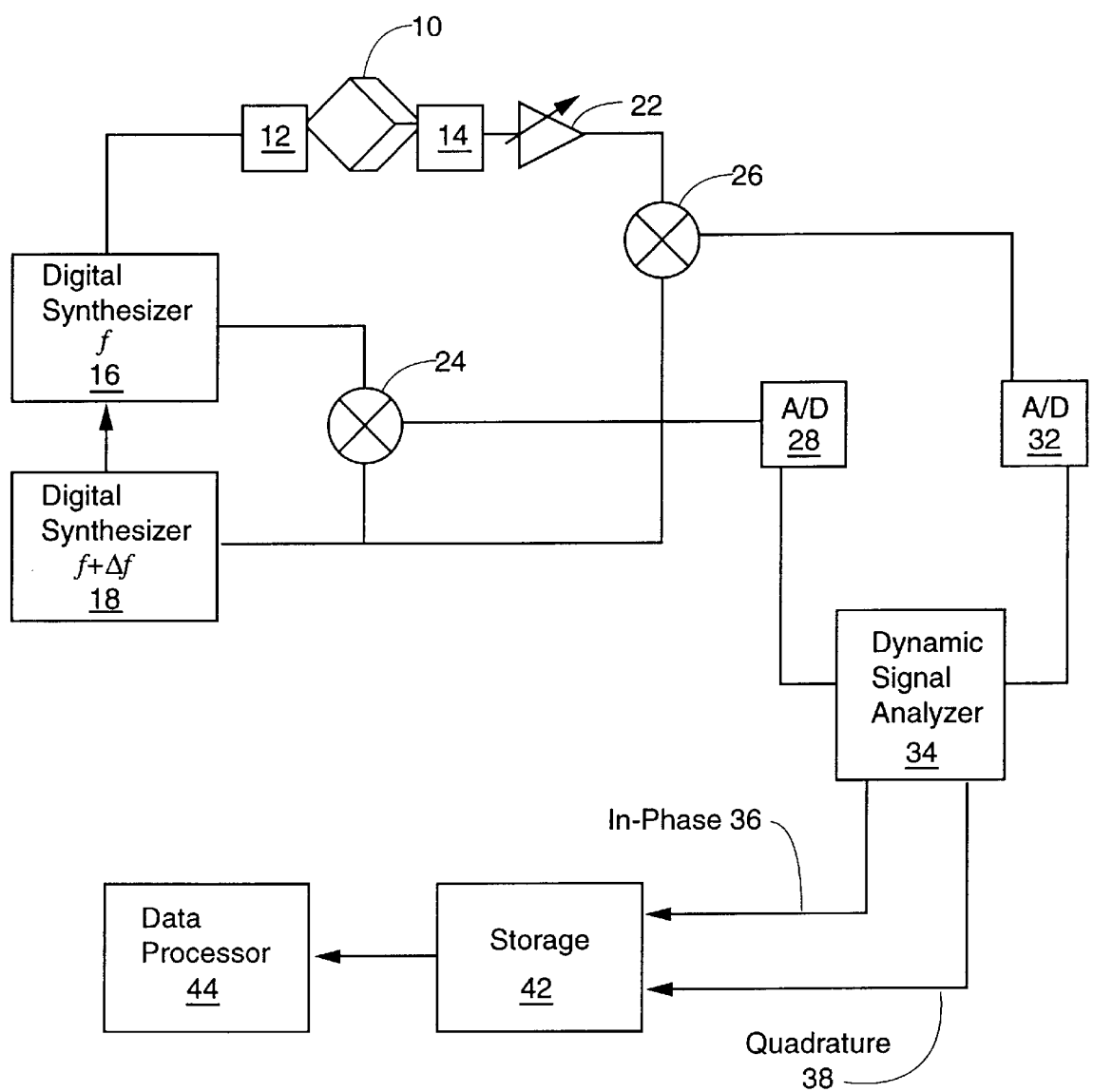
FIG. 2 is a schematic in block diagram form of one embodiment of a system for determining separate in-phase and quadrature components of a sample resonance response.

FIG. 2 is a block diagram schematic of an electronic system for acquiring and processing resonance response data according to one embodiment of the present invention. Sample 10 is contacted by an input transducer 12 for inputting an exciting acoustic signal to sample 10. The exciting mechanical input ultrasonic acoustic signal is generated by digital frequency synthesizer 16 that outputs a radio frequency (rf) signal, typically in a range of 5 kHz to 8 MHz. Synthesizer 16 may be controlled to sweep the exciting frequency in a specified range of frequency steps that are applied to sample 10.

In a preferred embodiment of the present invention, signal processing uses frequency mixing in superhetrodyne mixers 24, 26. Accordingly, digital frequency synthesizer 18 generates a frequency sweep in step with synthesizer 16 but at a frequency that is offset a constant IF frequency Δf (e.g., about 1 kHz) from the exciting frequency from synthesizer 16.

The response of sample 10 to the exciting signal from transducer 12 is detected by transducer 14, which outputs a response electrical signal to amplifier 22. Amplifier 22 is selected to obtain peak response outputs that are limited to appropriate system parameters (e.g., to less than +10 V in a preferred embodiment). The amplified response is then input to mixer 26 with the IF-offset rf output from synthesizer 18. The rf output from synthesizer 16 is input to mixer 24 with the output from synthesizer 18.

The output from mixer 26 is the IF difference frequency between the two input frequencies, i.e., Δf modified by the phase and amplitude of the response output from sample 10. The response IF output is input to analog-to-digital (A/D) converter 32 to output a digital signal for processing. The output from mixer 24 is the constant IF frequency, Δf, which is input to A/D converter 28 to provide a digital IF frequency signal to digital signal analyzer 34 for processing. In preferred embodiments, A/D converters 28, 32 sample at a 64 kHz rate and provide 16-bit digital outputs.

Dynamic signal analyzer 34 may be a conventional swept-sine spectrum analyzer (e.g., Hewlett Packard model HP89410A vector signal analyzer; Neel Model DSA-100) that separates the IF response signal into its in-phase component 36 (Re component as illustrated in FIG. 1) and quadrature component 38 (Im component as illustrated in FIG. 1). In another embodiment, functional components may be custom fabricated to perform only the functions that are needed to provide the process described herein. The in-phase 36 and quadrature 38 components are output and recorded at each of the discrete frequency steps during the frequency sweep across sample 10. The separated signal components 36 and 38 may be stored in a memory 42 for acceptance/rejection processing by data processor 44, which may be a programmed general purpose computer or a dedicated processor.

Figure 3A:
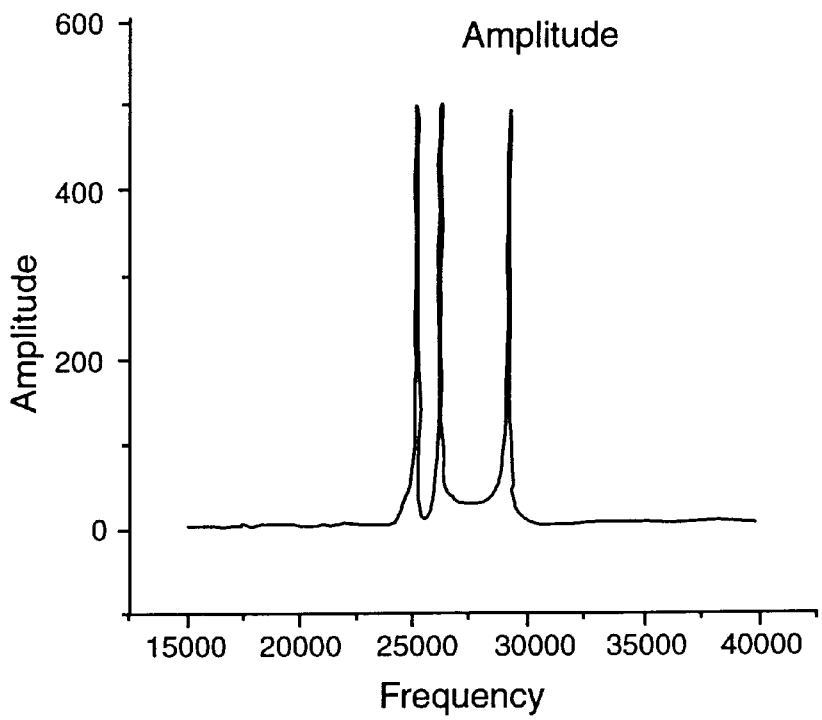
FIGS. 3A and 3B graphically depict amplitude and in-phase resonance responses for a good sample.
Figure 3B:
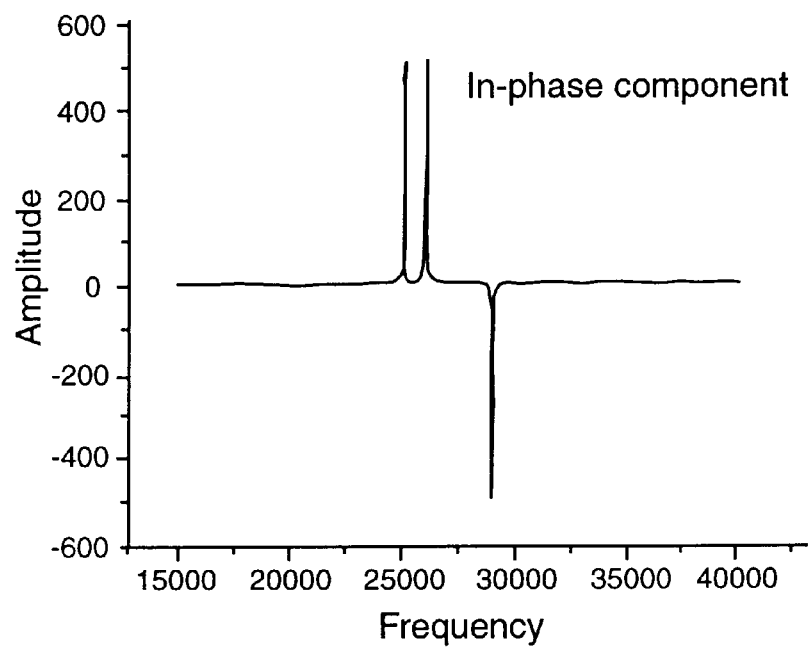
Figure 4A:
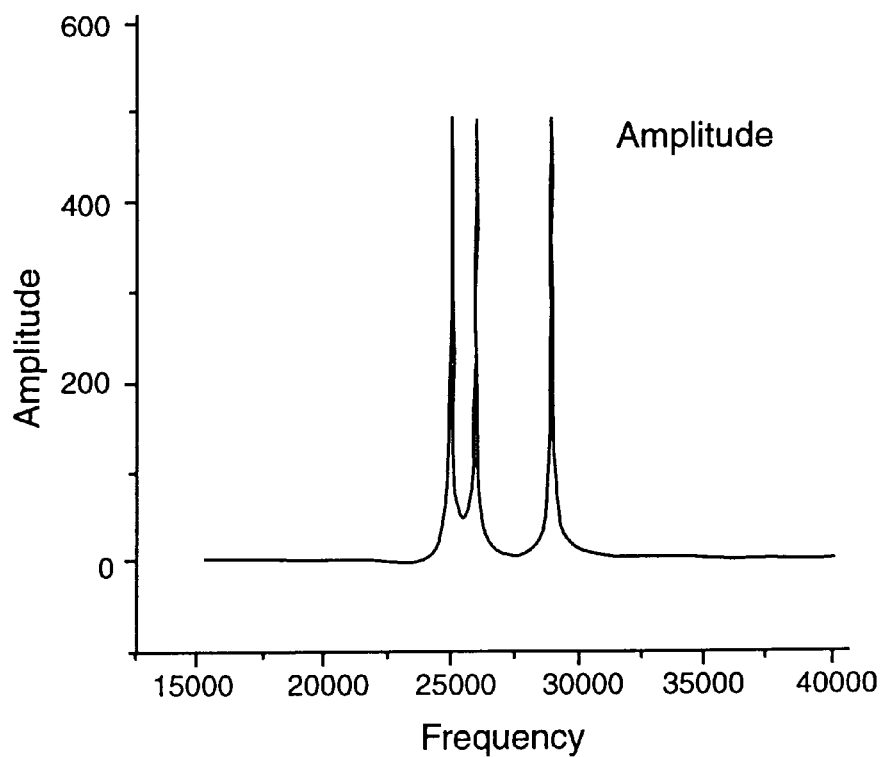
FIGS. 4A and 4B graphically depict amplitude and in-phase resonance responses for an unacceptable sample.
Figure 4B:
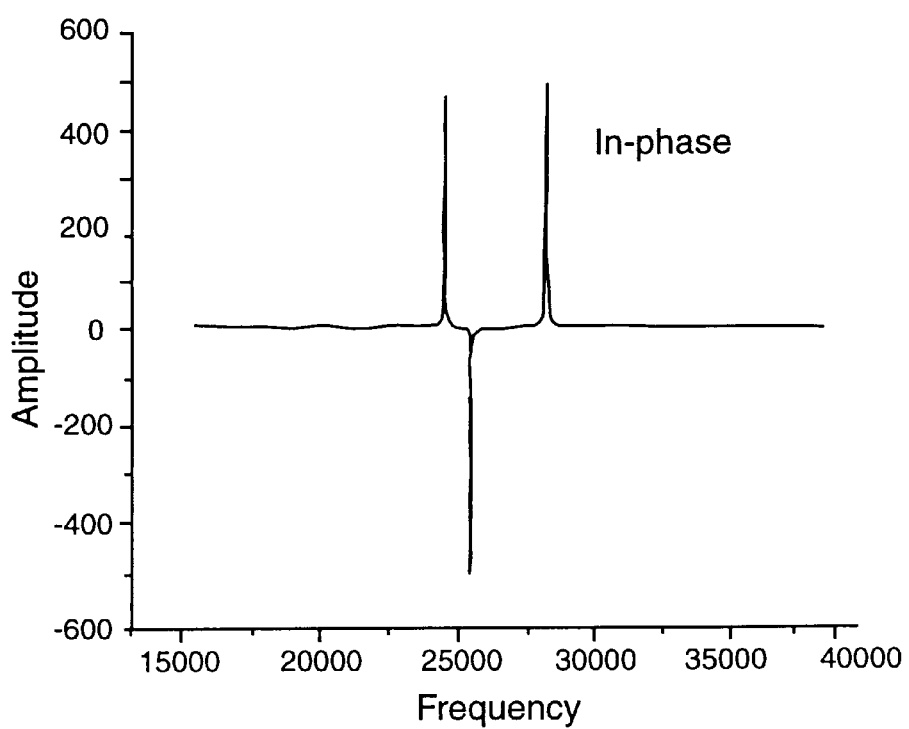

FIGS. 3A, 3B, 4A, and 4B illustrate one of the important features of the present invention, where the use of phase information to provide a separated in-phase response permits a more positive identification of resonance responses and of changes in the resonance responses arising from changing component characteristics. Exemplary FIGS. 3A and 3B depict the amplitude response and in-phase response, respectively, of a "good" part, i.e., a part deemed to be acceptable for its intended use. Three resonant responses are shown, where the two responses on the left have the correct separation and the response on the right is irrelevant to the acceptance criteria. FIG. 3B shows that the two relevant responses are in-phase, while the irrelevant response is out of phase with the relevant responses. FIGS. 4A and 4B provide the amplitude response and in-phase response of a "bad" part. Note that the amplitude response seen in FIG. 4A is substantially similar to the amplitude response seen in FIG. 3A. But FIG. 4B shows that the irrelevant response has moved toward the left-most amplitude resonance, while one relevant response has moved to the right. An inspection system using only an amplitude resonance response would accept both parts, while a phase-sensitive system according to the present system would correctly identify and reject the bad part.

In the phase-sensitive system, the phase information enables the resonance response peaks to be correctly identified. Where closely spaced resonance responses are present in a response spectrum, the phase information enables the relevant responses to be positively identified for use in framing acceptance/rejection criteria in a production RUS NDT test.

In another aspect of the present invention, knowledge of the in-phase and quadrature components enables a more accurate determination of the center frequency for a resonance by eliminating the problem of a coherent background and providing a symmetric resonance response curve in preparation for the application of sorting algorithms. A coherent background is a real response of the hardware to vibrations or electrical leakage via imperfect shielding of noise at the electronics input. Because of the great sensitivity required for resonance hardware, such a background is common and expensive or impossible to eliminate. An amplitude-only system irretrievably discards information and it is not possible to remove unambiguously a background response using software. In accordance with the present invention, in-phase information is available, however, and the background can be accurately removed using software.

Likewise, the use of in-phase and quadrature information enables a center response frequency to be accurately determined by computing the first moment for the response curve. The first moment is the sum of the products of frequency and the measured quantity (amplitude, in-phase component, or quadrature component) taken at each frequency step divided by sum of the measured quantity (amplitude, in-phase component, or quadrature component) taken at each frequency. In order to compute the first moment, however, the symmetric shape of the response must be preserved.

The resonance symmetry can be recovered by maximizing the first moment of the in-phase resonance response component as a function of rotation angle. The measured in-phase and quadrature response components are resolved along a plurality of rotation angles where the rotation angle forms the reference for new axes. That is, the new in-phase component is the sum of the cosine of the selected rotation angle times the measured in-phase component plus the sine of the selected rotation angle times the measured quadrature component. A new quadrature component is determined by interchanging the sine and cosine values in this equation. The first moment of the in-phase component is computed for each selected rotation angle and a rotation angle is selected that maximizes the first moment.

Figure 5A:
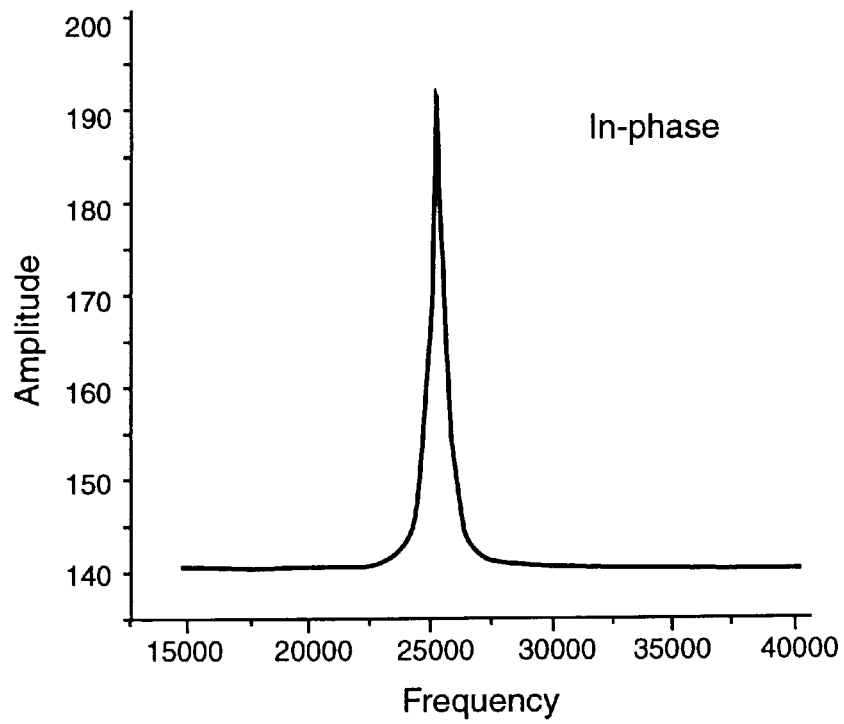
FIGS. 5A and 5B graphically depict symmetric and uncorrected peak resonance responses.
Figure 5B:
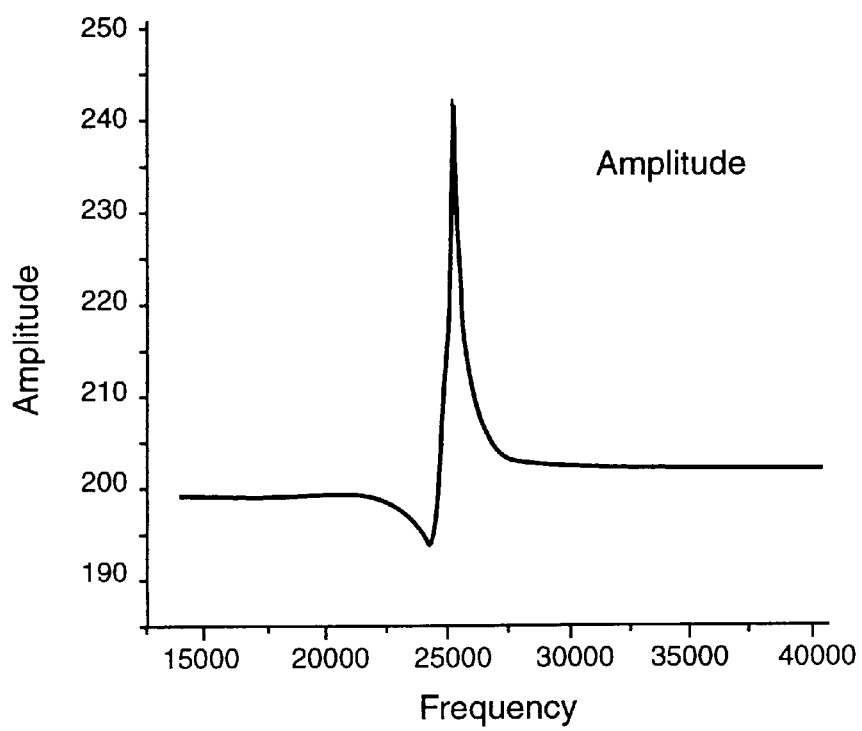

FIGS. 5A and 5B illustrate the results of adjusting an angle of rotation to provide a maximum first moment for the in-phase resonance response. FIG. 5B is the resonance response of a measured component in an amplitude sensitive system. The unsymmetrical nature of the response is apparent. FIG. 5A is a symmetrical response for the same component in a phase-sensitive system, where the overall phase has been adjusted by rotating the in-phase and quadrature responses to yield a maximum first moment for the in-phase resonance response.

Coherent background is removed by noting that the tails of each resonance (that is, data taken far from the central peak) consists almost entirely of background information. Thus, the in-phase and quadrature values in the tails completely define the background, enabling the background response to be readily removed. In the present process, Rex($\omega$) and Imx($\omega$) are averaged over a specified background and noise computation interval to obtain an in-phase average background and a quadrature average background. The background in-phase and background values are then subtracted from all of the in-phase and quadrature data, respectively.

Once the background is removed, the width of the resonance can be more accurately determined. The width is 2/($\pi$amax) times the sum over the in-phase and symmetrized waveform of the frequency times the in-phase component where amax is the height of the peak. The width of the resonance is a direct measure of Q, a useful quantity for NDT.

Figure 6:
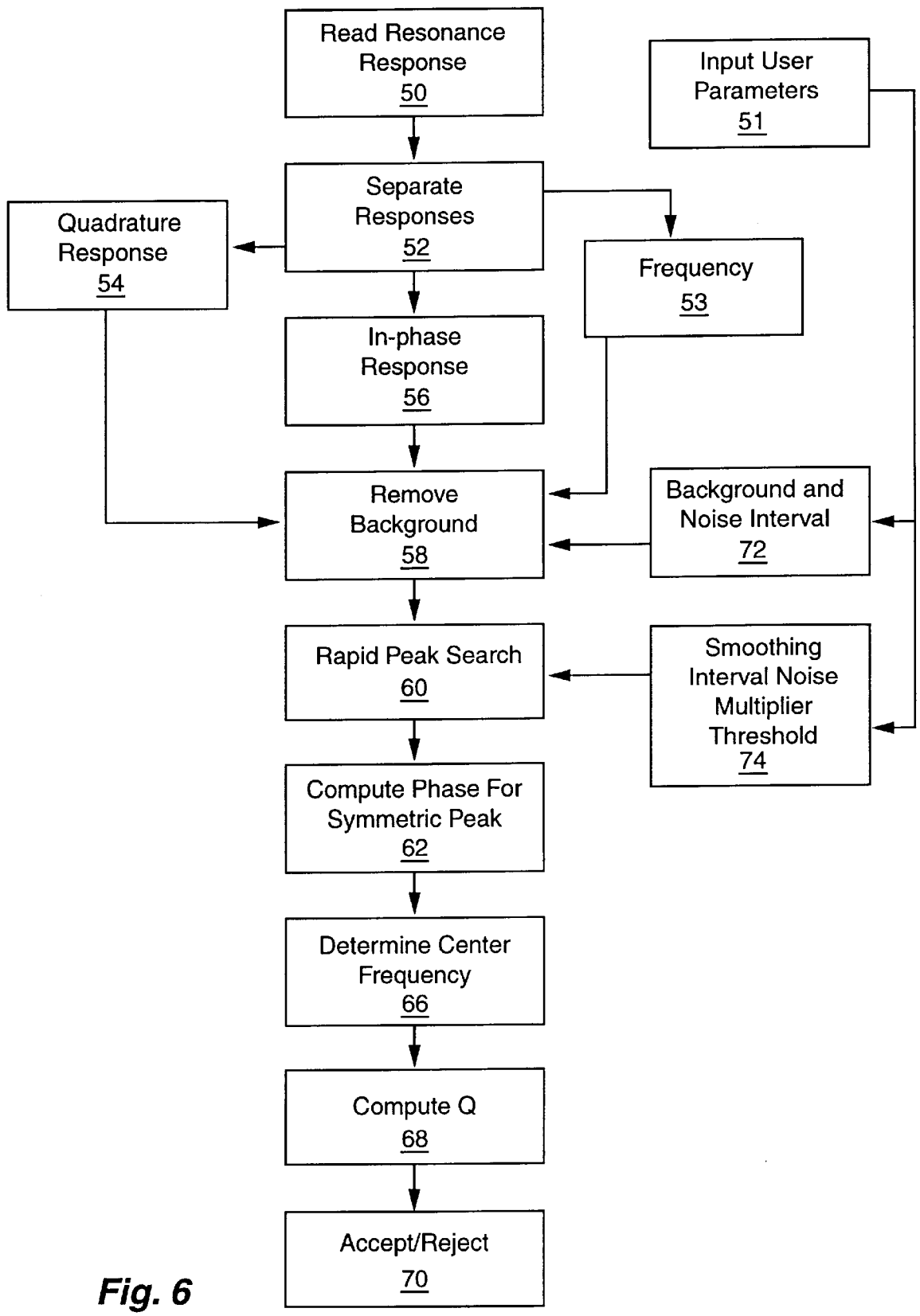
FIG. 6 is a flow chart of an exemplary process for correcting for background noise and for providing symmetric in-phase peak responses.

FIG. 6 is a flow chart of the above signal processing to provide response characteristics that are useful in RUS NDT evaluation. The sample response characteristics are digitized for input 50 to a dynamic system analyzer (see analyzer 34 in FIG. 1). The analyzer then separates 52 the response into a quadrature response 54 and an in-phase response 56 and outputs the associated frequency 53 for each data point. In a preferred process, various user selected parameters 51 are also input. Typical user parameters include (a) a smoothing interval for use in data smoothing; (b) multiplier for auto threshold to provide an adjustable sensitivity; (c) a threshold multiplier for a preliminary Q determination; (d) width and location for taking the background and noise computation sample; (e) auto-phase computation interval for determining a symmetric response. It will be appreciated that these parameters depend on the expected response spectrum for any given component and are experimentally selected to provide an optimum response for accepting/rejecting such components.

Quadrature response 54, in-phase response 56, and frequency 53 data are input to background removal processor 58 for the removal of coherent background response information. The in-phase response data and the quadrature response data are averaged at the selected location for background and noise computation 72 and the data are averaged over a selected frequency interval. The selected location is remote from the location of expected response peaks in the respective data.

In accordance with the present invention, the location of response amplitude peaks are first determined 60 so that the data around the frequency of the peaks can be processed to provide symmetric response curves for further processing. The in-phase data is smoothed, i.e., averaged, over a succession of smoothing intervals 74. A background and noise threshold is computed from computed root-mean-square (RMS) values of the in-phase signal over the noise and background computation interval and is multiplied by a selected multiplier 74 to provide a threshold amplitude. The smoothed data is then monitored to determine amplitude values above the threshold to locate amplitude values indicative of a possible peak. This process eliminates spurious noise peaks from examination. The amplitude values above the threshold are then examined for a positive slope until a zero slope is detected. The frequency location for a zero-slope determination is stored as a peak location. For each peak, the frequency separation between the curve locations having a value of 0.707 of the peak value and an initial Q value is computed as the frequency at the peak amplitude divided by the determined frequency separation. The initial Q value is saved to a file.

The peak response curve is then processed to adjust a rotation phase angle 62 and output-adjusted in-phase response data as a symmetric peak response. As noted above, the phase angle is determined by resolving the in-phase response and associated quadrature response along various phase angles until a maximum in a computed first moment for the peak response curve. Once a peak is located, the function Y(f)=Re(f)cos$\theta$+Im(f)sin$\theta$ is integrated over the region of the peak response that is selected by the user. The integration is repeated as a function of the phase angle $\theta$ until a maximum value is obtained. This angle is designated as the "auto-phase" angle for that peak response. It will be appreciated that each response peak will have its own auto-phase angle.

From the auto-phase angle of the peak, a center frequency is determined 66 that can be used for product acceptance/rejection 70. The function $$Y(f)=Re(f)\cos\theta+Im(f)\sin\theta$$

is first computed over a frequency around the peak that is specified by the user. The center frequency of the peak is then determined from $$f_{center} = \frac{\int Y(f) * f\, df}{\int Y(f)\, df}.$$

The Q of the peak response is determined 68 from $$Q = f_{center} \frac{\pi * amax}{2} \frac{1}{\int Y(f)\, df}.$$

The values for $f_{center}$ and Q are stored in a file for later use in accepting/rejecting the component being examined.

Various acceptance/rejection criteria can be formulated from the peak and phase information provided by the above analysis. Some exemplary criteria include:

1. Determine the resonant frequency peaks that appear within a given test windows and compare with the peaks from an acceptable part.

2. Establish a test window that includes a single peak and determine if the sample has a resonance peak within the window.

3. Compare the amplitude of the peaks in a test window with the amplitude of reference peaks within the window.

4. Compare the separations of peaks within the test window with the separation of reference peaks within the window.

It should be understood that many more criteria may be established from the generated information and that the above criteria are merely exemplary. The selection of acceptance/rejection criteria will be determined by the RUS characteristic of acceptable components. Once these characteristics are established, then unacceptable deviations can be specified for an automated examination process.

Figure 7A:
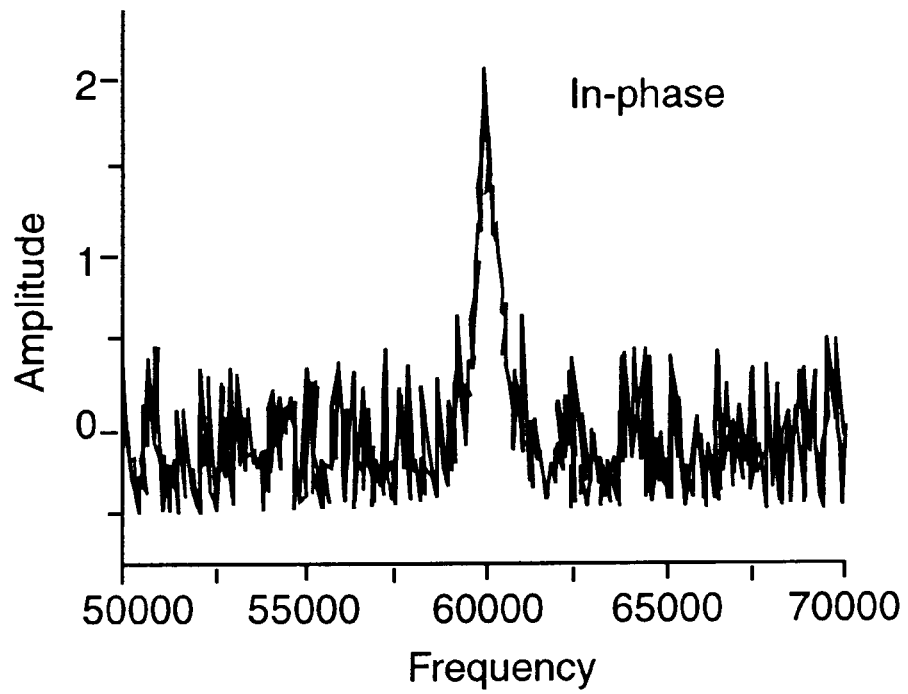
FIGS. 7A and 7B graphically depict data corrected for background noise and to provide a symmetric resonance response peak and the raw resonance data used to derive the corrected data.
Figure 7B:
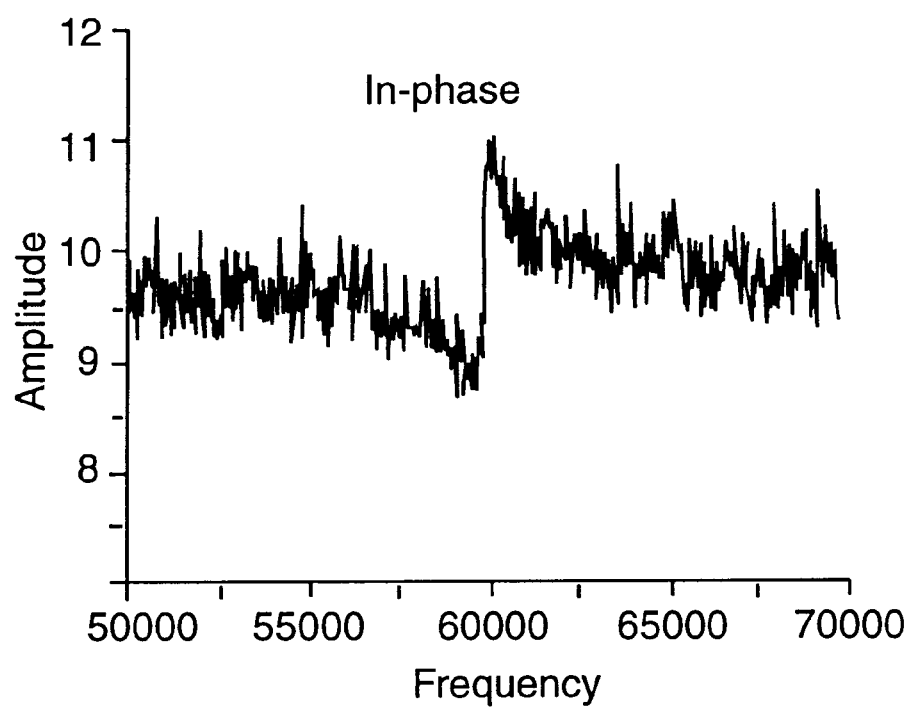

It will be appreciated that the center frequency can be more readily determined once the background is removed from the in-phase data and the response has been made symmetric by rotation of the data in accordance with the present invention. More representative values for Q can also be determined from the symmetric response. FIGS. 7A and 7B illustrate this feature, where FIG. 7B is the raw scan of the in-phase component data with coherent background noise and asymmetrical peak. FIG. 7A is the same data with the background removed and the in-phase component rotated for a symmetric peak. Once the peaks are adjusted to be symmetric, peak finding algorithms have only one type of pattern to search for a more rapid determination of peak location. For example, a peak finder routine that first computes a noise background, then looks for a positive slope above a threshold determined by the noise, then looks for a negative slope, can be made to operate very rapid and accurately.

The foregoing description of the invention has been presented for purposes of illustration and description and is not intended to be exhaustive or to limit the invention to the precise form disclosed, and obviously many modifications and variations are possible in light of the above teaching.

The embodiments were chosen and described in order to best explain the principles of the invention and its practical application to thereby enable others skilled in the art to best utilize the invention in various embodiments and with various modifications as are suited to the particular use contemplated. It is intended that the scope of the invention be defined by the claims appended hereto.

What is claimed is:

1. A method for determining relevant resonance response characteristics for use in characterizing a sample, including the steps of:

generating a response of said sample to an exciting mechanical input at a plurality of ultrasonic frequencies;

separating said response into in-phase and quadrature components; and computing symmetric modified in-phase resonance response characteristics from said in-phase and quadrature components to characterize said sample.

2. A method according to claim 1, wherein the step of generating said response of said sample further includes the steps of:

inputting an exciting rf signal frequency to said sample;

generating a modified rf signal at said exciting rf frequency offset by a constant IF value;

mixing said modified rf signal with said response of said sample to output a response IF signal that includes phase and amplitude characteristics of said response of said sample; and mixing said modified rf signal with said exciting rf signal to output said constant IF value.

3. A method according to claim 1, wherein the step of computing said symmetric modified in-phase resonance response characteristics further includes the step of:

selecting from said in-phase components of said response relevant resonance responses for use in accepting or rejecting said sample.

4. A method according to claim 1, wherein the step of computing said symmetric modified in-phase resonance response characteristics further includes the step of removing background response noise from said response of said sample.

5. A method according to claim 1, wherein the step of computing said symmetric modified in-phase resonance response characteristics further includes the steps of:

projecting said in-phase and quadrature components onto axes that are rotated through a plurality of rotation angles to output a modified in-phase response at each one of said rotation angles;

computing a first moment of each said modified in-phase response; and selecting one of said rotation angles that produces a maximum said first moment to provide said symmetric modified in-phase response characteristic.

6. A method according to claim 2, wherein the step of computing said symmetric modified in-phase resonance response characteristics further includes the steps of:

projecting said in-phase and quadrature components onto axes that are rotated through a plurality of rotation angles to output a modified in-phase response at each one of said rotation angles;

computing a first moment of each said modified in-phase response; and selecting one of said rotation angles that produces a maximum said first moment to provide said symmetric modified in-phase response characteristic.

7. A method according to claim 1, further including the step of finding a center frequency for said modified in-phase response characteristic.

8. A method according to claim 1, further including the step of finding a peak amplitude value for said modified in-phase response characteristic.

9. A method according to claim 8, further including the step of finding a Q value for said modified in-phase response characteristic.

10. Apparatus for determining relevant resonance response characteristics for use in characterizing a sample, said apparatus comprising:

a frequency generator for inputting an exciting ultrasonic frequency to said sample;

a transducer for outputting a response of sample to said exciting ultrasonic frequency;

a dynamic signal analyzer connected to receive said response of said sample and to output in-phase and quadrature components of said response of said sample; and a computer for determining said relevant response characteristics from said in-phase and quadrature components, where said computer is electrically configured to provide a symmetric in-phase characteristic for said response signal.

11. Apparatus according to claim 10 wherein said frequency generator further comprises:

a first frequency synthesizer for outputting a rf exciting frequency signal;

a second frequency synthesizer for outputting a modified rf signal at said rf exciting frequency offset by a constant IF signal;

a first mixer for mixing said response of said sample with said modified rf signal to output a response IF signal that includes phase and amplitude characteristics of said response of said sample; and a second mixer for mixing said modified rf signal with said exciting frequency signal to output said constant IF value.

12. Apparatus according to claim 10, where said computer is electrically configured to remove coherent background noise from said response of said sample.

13. Apparatus according to claim 10, where said computer is electrically configured to provide a center frequency for said symmetric in-phase characteristic.

14. Apparatus according to claim 10, where said computer is electrically configured to provide a peak amplitude value for said symmetric in-phase characteristic.

* * * * *